US009295492B2

(12) United States Patent
Dorawa (10) Patent No.: US 9,295,492 B2
(45) Date of Patent: Mar. 29, 2016

(54) FIXATION CLAMP

(71) Applicant: Stryker Trauma SA, Selzach (CH)

(72) Inventor: Klaus Dorawa, Schoenkirchen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 133 days.

(21) Appl. No.: 13/706,924

(22) Filed: Dec. 6, 2012

(65) Prior Publication Data

US 2013/0144289 A1 Jun. 6, 2013

(30) Foreign Application Priority Data

Dec. 6, 2011 (EP) ..................................... 11192152

(51) Int. Cl.
*A61B 17/00* (2006.01)
*A61B 17/60* (2006.01)
*A61B 17/64* (2006.01)

(52) U.S. Cl.
CPC ............. *A61B 17/60* (2013.01); *A61B 17/6466* (2013.01)

(58) Field of Classification Search
USPC ................................ 606/53–59; 411/533, 539
See application file for complete search history.

(56) References Cited

U.S. PATENT DOCUMENTS

| 857,227 | A | * | 6/1907 | Booth | ........................... 411/354 |
|---|---|---|---|---|---|
| 1,611,567 | A | * | 12/1926 | Sonen | ........................... 411/539 |
| 5,197,841 | A | * | 3/1993 | Tanaka | ........................... 411/522 |
| 5,380,325 | A | * | 1/1995 | Lahille et al. | ................. 606/250 |
| 6,080,153 | A | | 6/2000 | Mata et al. | |
| 2009/0148232 | A1 | * | 6/2009 | Thomke et al. | ............... 403/373 |
| 2009/0299368 | A1 | * | 12/2009 | Bauer | .............................. 606/57 |
| 2010/0298827 | A1 | * | 11/2010 | Cremer et al. | ................... 606/54 |
| 2011/0066151 | A1 | * | 3/2011 | Murner et al. | .................. 606/54 |
| 2011/0087226 | A1 | * | 4/2011 | Murner et al. | .................. 606/54 |
| 2011/0098707 | A1 | * | 4/2011 | Mullaney | ........................ 606/59 |
| 2012/0089142 | A1 | * | 4/2012 | Mullaney et al. | ............... 606/54 |
| 2012/0093611 | A1 | * | 4/2012 | Knight, Jr. | .................... 411/368 |
| 2012/0150181 | A1 | | 6/2012 | Dorawa et al. | |
| 2012/0150182 | A1 | | 6/2012 | Dominik et al. | |
| 2012/0150183 | A1 | | 6/2012 | Dorawa et al. | |

FOREIGN PATENT DOCUMENTS

EP 2294994 A1 3/2011
EP 2294995 A1 3/2011

OTHER PUBLICATIONS

European Search Report for EP 11 192 152.4 dated Apr. 16, 2012.

* cited by examiner

*Primary Examiner* — Jan Christopher Merene
*Assistant Examiner* — Steven Cotroneo
(74) *Attorney, Agent, or Firm* — Lerner, David, Littenberg, Krumholz & Mentlik, LLP (57) ABSTRACT

A fixation clamp for use in an external fixation clamp has a clamping assembly having a reception to accommodate a fixation element. The clamp has a locking element extending through the clamping assembly for blocking the position in a defined angular position. A washer is arranged between the locking element and a central opening of the clamping assembly having a cutout extending radially from the through opening such that the washer is mountable and demountable in a radial direction to a locking element longitudinal axis. The cutout has a smaller distance between its sidewalls then the diameter of the through opening. The locking element has circular cross-section below its head portion adapted to fit through the through opening of the washer but larger than the opening of the cutout and has at least one pair of parallel beveled surfaces spaced closer than the distance between sidewalls of the washer cutout.

24 Claims, 4 Drawing Sheets

FIXATION CLAMP

CROSS-REFERENCE TO RELATED APPLICATION

The present application claims priority from European Patent Application No. 11192152.4 filed Dec. 6, 2011, the disclosure of which is hereby incorporated herein by reference.

BACKGROUND OF THE INVENTION

The present invention relates to a fixation clamp, more particularly to a fixation clamp for use in an external fixation system for holding bone fragments adjacent to each other with the help of fixation elements, comprising at least one clamping assembly having at least one reception to accommodate a fixation element along the longitudinal axis of the reception and at least one locking element extending through the clamping assemblies for blocking the position of the clamping assemblies in a defined angular position, wherein between said locking element and said at least one clamping assembly there is arranged a washer.

External fixation systems are widely used to connect two or more bone fragments to each other. Such systems comprise bone screws, pins, wires which are inserted directly into the bone material and these systems use external structural elements as fixation rods, bars and rings. In order to connect the rods and bars to form a rigid frame, fixation clamps are used. Furthermore, fixation clamps are used to connect this screws and pins to the rigid frame to specifically hold bone fragments at an intended place. One adjustable fixation clamp of such a kind is known from U.S. Pat. No. 6,080,153 comprising two pairs of jaws allowing clamping of a rod as well as of a pin.

U.S. Patent Application Publication No. 2010/0298827 discloses a further fixation clamp having the features of the preamble of claim 1. Users feel very comfortable with the fixation clamp according to U.S. Patent Application Publication No. 2010/0298827. However, there is a need to have a fixation clamp which can be cleaned more easily and which can also compensate angular orientation between the rods or pins during the mounting process. Furthermore the handling during the cleaning steps should be improved.

U.S. Patent Application Publication No. 2012/0150183 relates to a fixation clamp having a jaw with a convex surface with a washer thereon. The disclosure of U.S. Patent Application Publication No. 2012/0150183 is incorporated herein by reference.

BRIEF SUMMARY OF THE INVENTION

It is one aspect of the present invention to provide a fixation clamp which overcomes the disadvantages of prior art. It is in particular an object of the present invention to provide a fixation clamp which can be more easily handled during the preparation of cleaning steps while it remains fully adjustable during the mounting process. It is a further aspect of the present invention to provide a fixation clamp which is dismountable for cleaning purposes in a very easy manner. This aspect is achieved by said washer which is dismountable in a direction substantially perpendicular to said locking element.

This one aspect can be achieved by a fixation clamp, more particularly for use in an external fixation system for holding bone fragments adjacent to each other with the help of fixation elements, comprises at least one clamping assembly having at least one reception to accommodate a fixation element along the longitudinal axis of the reception and at least one locking element extending through the clamping assemblies for blocking the position of the clamping assemblies in a defined angular position. Between said locking element and said at least one clamping assembly there is arranged a washer comprising a central through opening and a cutout extending radially from said through opening such that said washer is mountable and demountable in essential radial direction to the middle axis of the locking element. The cutout has a smaller distance between its sidewalls then the diameter of the through opening. The locking element has an essentially circular cross-section below its head portion adapted to fit through the through opening of the washer but larger than the opening of the cutout and comprises at least one pair of beveled surfaces parallelly oriented one to the other and having a distance one from the other being smaller than the distance between the sidewalls of the cutout of the washer.

In particular it shall be prevented that the fixation clamp has to be dismounted in a complicated manner and/or that all of the parts of the fixation clamps have to be separated. This object is achieved by an abutment surface. The bore comprises towards the contact surface preferably a first diameter which is adjoined by a second diameter, wherein the first diameter is larger than the second diameter such that between the first and the second diameter an abutment surface is provided, which abutment surface serves as abutment element for the locking element, in particular for flange, in case the washer is removed.

A user of the fixation clamp can then apply a method for mounting or removing such a washer on or from the fixation clamp. There is provided at least one clamping assembly having at least one reception to accommodate a fixation element along the longitudinal axis of the reception and at least one locking element extending through the clamping assemblies for blocking the position of the clamping assemblies in a defined angular position. Furthermore is provided a washer having a central through opening having a middle axis, having a cutout extending radially to said middle axis of said through opening, wherein the cutout has a smaller distance between its sidewalls then the diameter of the through opening. Then the locking element has an essentially circular cross-section below its head portion adapted to fit through the through opening of the washer but larger than the opening of the cutout and wherein the locking element comprises at least one pair of beveled surfaces parallelly oriented one to the other and having a distance one from the other being smaller than the distance between the sidewalls of the cutout of the washer. The washer is turned or rotated around its axis for mounting the washer onto the shaft of the locking element or removing the washer from the shaft of the locking element, respectively, so that the radial direction of the cutout is oriented in parallel to the beveled surfaces of the locking element. Then the washer is pushed with its cutout in an essentially radial direction towards the middle axis of the locking element for mounting and it is pulled with its cutout in an essential radial direction from the middle axis of the locking element for removing. Optionally, the turning step comprises orienting a marking indicating either the direction of one or the pair of beveled surfaces, preferably provided on the upper surface on the head of the locking element, or one or more markings on a side of the head, so that the cutout portion of the washer to be inserted or removed is oriented in the same direction as the marking.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
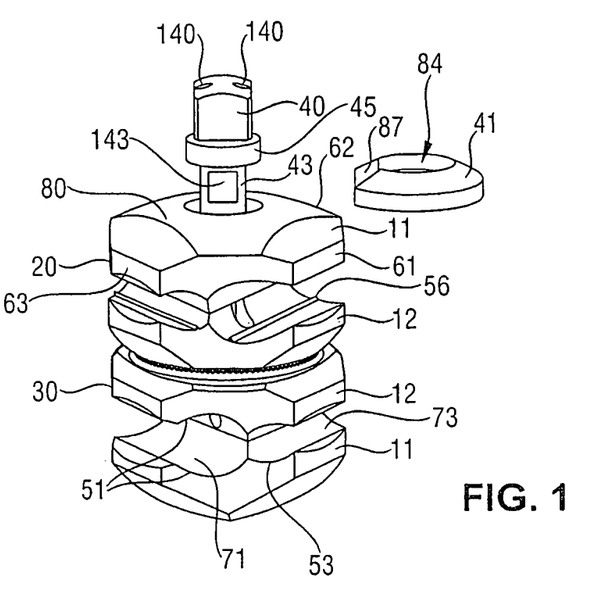
FIG. 1 shows a perspective view of an embodiment of a fixation clamp of the present invention during mounting of its washer.
Figure 2:
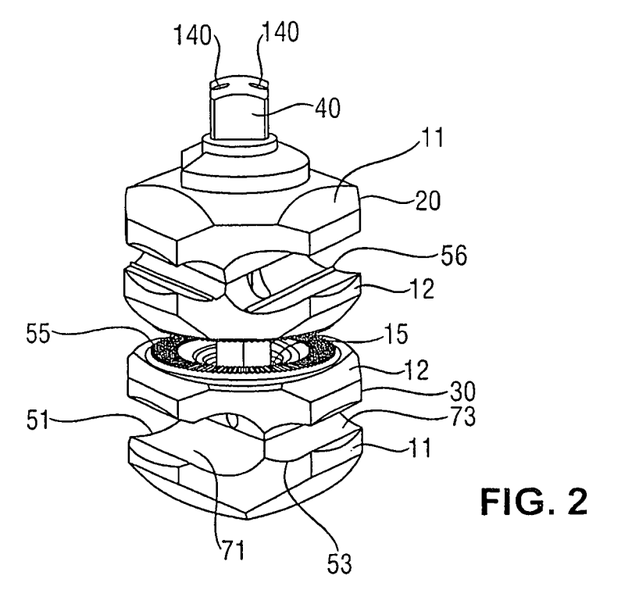
FIG. 2 shows a perspective view of the fixation clamp of FIG. 1 in a released state.

FIG. 1 shows a preferred embodiment of a clamping element or fixation clamp 10 pursuant to the invention during mounting of its washer 41. As will be explained below, this relates to the opening of the locking element 40 to a certain extent, preferably to its maximum extent. FIG. 2 shows the embodiment of FIG. 1 in its released state. The term released state refers to the position possibility to introduce rods or pins into the receptions of the fixation clamp, here before a at least partial closing of the clamping element towards the mounted state. The partial closing relates to the reduction of the gap G between the two clamping assemblies 20 and 30. The term mounted state refers to the possibility to introduce rods or pins into the receptions of the fixation clamp as explained below.

The clamping element 10 consists of a first clamping assembly 20 and a second clamping assembly 30 and a locking element or shaft 40 which is positioned through bores (bore 31 can be seen in FIG. 3) within the two clamp assemblies 20, 30 along the longitudinal axis M of shaft 40. Shaft 40 is preferably a locking element adapted to allow closing the clamp assemblies 20 and 30. Shaft 40 enters a first jaw 11 through a washer 41.

The shaft 40 comprises a head portion 44, a reduced diameter portion 43 which is followed by a shaft portion and a thread portion. This sequence of head 44, followed by a flange 45 and the reduced diameter 43, followed by a shaft and a final thread portion located in the lowest jaw 11 can be provided as disclosed in EP 2 250 968 in the name of the present applicant (see the cross-section of FIG. 7 reflecting the same sequence). The outer threaded portion 49 is adapted to be screwed into a complementary inner thread within the distal jaw 11 so that turning the head of the shaft 40 changes the longitudinal position of the shaft 40 against the lower jaw 11, which allows opening or closing the entire clamp 10 against the force of a spring 15 provided between the two clamp assemblies 20 and 30. Said spring 15 is preferably positioned in corresponding receptions 16 in the jaws 12. Instead of a spring 15, provided around shaft 40, it is possible to provide a different spring means as Belleville washers or an elastic compressible solid or foam. Upon closing of the clamp assemblies 20 and 30 the jaws 12 adjacent to the spring 15 can eventually come into contact and then the anti-rotation surfaced 55 which are provided in both surfaces of the jaws 12 fix the angular orientation of each clamping assembly 20 and 30 against the other.

Preferably after having mounted the shaft 40 with the thread 49 within the lower jaw 11, the end portion of the thread is destroyed through pressure to ensure that the shaft 40 cannot be removed from the clamping assemblies 20, 30 to maintain the clamp as one single piece.

Each clamping assembly 20 or 30 comprises two opposing clamping jaws 11 and 12. These jaws 11 and 12 are essentially similarly shaped on the sides facing each other. Each of the jaws 12, 11 comprises a respective contact surface 18, 19 facing the other surface of the jaw 11, 12.

In order to prevent rotation between the jaw 11 and the jaw 12 as well as in order to prevent a misalignment of the jaw 11, 12 at least one orientation device 13, 14 is arranged on the surfaces 18, 19. In the present embodiment in the second clamping assembly 30 the jaw 11 comprises an opening 14 extending into surface 18 and the jaw 12 comprises a pin 13 extending from surface 19. The pin 13 extends into the opening 14. This pin-opening connection prevents therefore a possible rotation between the jaws 11, 12 and a possible misalignment between the jaws 11, 12.

The jaws 11 and 12 are provided here with three grooves 51, 52 and 53. Grooves 51, 52 and 53 are all provided in a same plane perpendicular to the longitudinal axis of shaft 40. In that plane they are oriented perpendicular to the radial direction from the center of the bore 21 or 31. As such the grooves 51, 52 and 53 are substantially parallel to outer side wall 61, 62 or 63 of each pair of jaws 11 and 12.

Each pair of grooves 51, 52 or 53, respectively, in each jaw 11 and 12, define one reception, i.e. a first reception 71, a second reception 72 and a third reception 73. The grooves 51, 52 and 53 are each formed as a rounded semi-spherical recess in section to provide receptions 71, 72 and 73 which accommodate cylindrical pins or rods with a defined diameter, if the clamp is closed. The outer side walls 61, 62 or 63 can comprise an inclined sliding surface to allow an easier clipping of such pins or rods 100 into the corresponding reception. The grooves 51, 52, 53 are called to form rounded semi-spherical recesses in a section. This means that the recesses provided by the grooves 51, 52, 53 have a hollow cylindrical shape to accommodate rod-shaped elements. Some or all of the grooves 51, 52, and 53 are also provided with friction enhancing elements such as ribs 56.

All three grooves 51, 52 and 53 have different sizes so that the corresponding receptions 71, 72 and 73 have three different sizes. In other words each reception 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 11 and 12 and these comprise three grooves 51, 52, 53. These grooves 51, 52, 53 also comprise a sequence of different sizes. In the embodiment shown the inner jaws portion 12 have an identical structure as have the outer jaws 11, especially in view of the anti-rotation device 55, the reception 16 for a spring 15.

Within a preferred embodiment the first clamping assembly 20 may comprise a sequence of smaller sizes, e.g. 7 mm, 5 mm and 3 mm; or 6 mm, 5 mm and 4 mm; and the second clamping assembly 30 may comprise a sequence of larger sizes, e.g. 13.5 mm, 12 mm and 10 mm. Different sizes are possible, usually for wires starting from 2 mm diameter until thicker rods with a diameter of 30 mm are used within such a clamp 10. Such a clamp allows using one single versatile clamp, wherein the first clamping assembly 20 is used to fix a specific pin or screw or wire having a diameter for which one of the receptions 71, 72 or 73 is adapted. The user takes the clamp 10 and orients the first clamping assembly 20 into the correct alignment so that the pin or screw can be clipped into the corresponding reception.

Then the clamp 10 can be clamped on a rod of an external fixator with the help of the second clamping assembly 30. Said second clamping assembly 30 can be oriented in a way so that the rod can be clipped into the corresponding reception. It is an advantage of the clamp 10 having two clamping assemblies 20 and 30 according to the invention, that a practitioner attaching such a clamp at a bone screw with one clamping assembly 20 and subsequently a rod of an external fixator to the other clamping assembly 30 can check the robustness of his external fixator, and if he finds that the rod he has used is not stiff enough, he simply opens the second clamping assembly 30, removes the thinner rod, turns the second clamping assembly 30 e.g. 60 degrees into one direction or the other around the longitudinal axis to align the larger reception with the new thicker rod and replaces it. This change does not necessitate the replacement of the clamp 10 itself as necessary with prior art systems. The method to replace such a rod is faster and more reliable since the clamping of the bone screw is not changed, and avoids use of a second sterile clamp at said time.

It is of course also possible that the second clamping assembly 30 is a traditional clamping assembly or even any other element known in the prior art with clamping elements. The object of a versatile clamping assembly is already achieved through one first clamping assembly 20, since it allows clamping one of three different sizes of screws, pins of wires through simple reorientation of the first clamping assembly 20.

Figure 3:
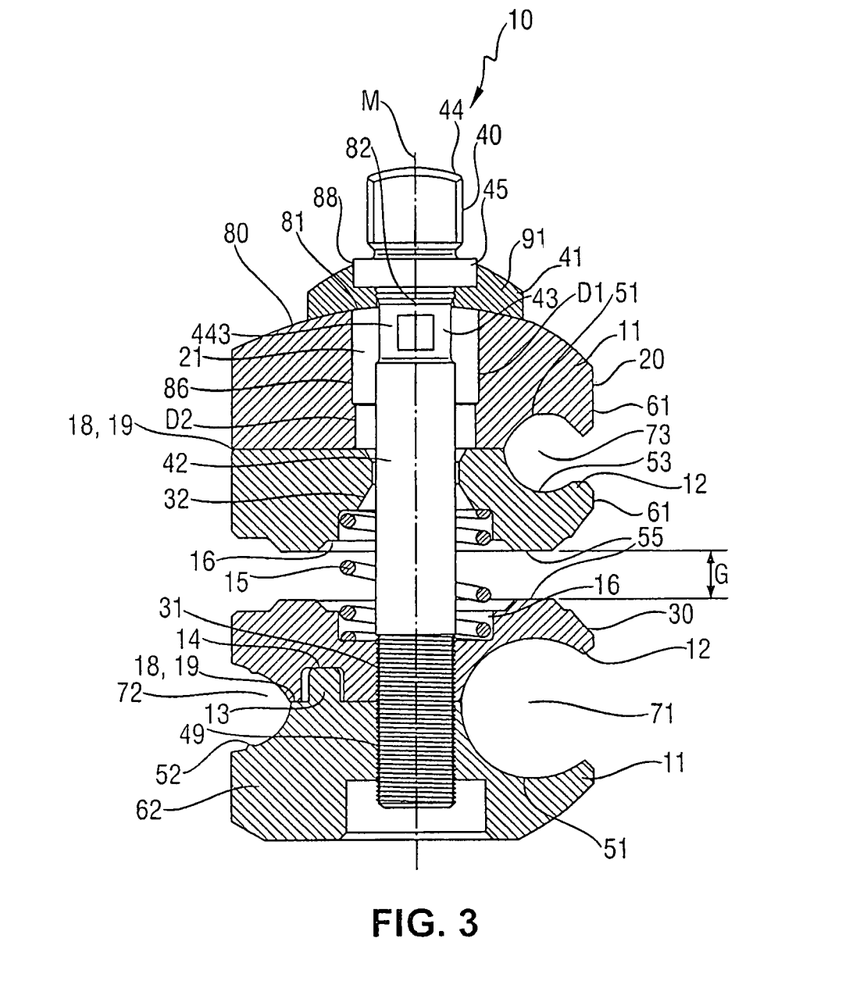
FIG. 3 shows a cross-section of the fixation clamp according to FIG. 1.

FIG. 3 shows a cross-section of the clamp according to FIG. 1, wherein the clamp 10 is shown in a premounted state, i.e. the spring 15 is under tension. Preferably the length of shaft 40 is chosen, so that spring 15 is always under tension, independent of the opening of the clamping assembly. The upper jaw 11 of the first clamping assembly 20 is therefore pushing the washer 41 against a flange 45 of the head of shaft 40. The bore 21 which accommodates part of the shaft portion 42 and the reduced diameter portion 43 is provided with a larger diameter than the respective diameter of the shaft 40 so that an angular or pivoting movement of the first clamping assembly 20 against the shaft 40 is possible. This is in particularly advantageous during the mounting process of the fixation clamp. With this regard it has to be noted that also bore 31 can be provided with a larger diameter than the respective section of the shaft 40 such that jaw 12 of the second clamping assembly becomes pivotable to the shaft 40.

The diameter D1, D2 of bore 21 of the first clamping assembly 20 is larger than the diameter of the locking element 40 extending through the bore 21. Thereby a pivoting movement or displacement between the locking element 40 and the first clamping assembly 20 during positioning the clamping assemblies 20, 30 and the pins or rods becomes possible. In the present embodiment the bore 21 in the first jaw 11 is a bore 21 having an abutment surface 86. The abutment surface 86 is provided by means a step-like bore 21 having a first section with a first diameter D1 and a second section with a second diameter D2. The first diameter D1 is larger than the second diameter D2. The abutment surface 86 serves as abutment element for the locking element 40 in particular for the flange 45 in case washer 41 is removed. Hence the abutment surface 86 together with the flange prevents that the first clamping assembly 20 will be separated from the second clamping assembly 30 when the washer is removed. Particularly during a cleaning or sterilization process the prevention of such a separation is very advantageous.

According to the embodiment shown in FIG. 3, the uppermost jaw cannot be removed from the shaft 40. It is possible to provide the uppermost jaw with a through bore of diameter D1 so that it can be removed.

Alternatively the bore 21 can be provided with a conical section 32 as shown with bore 21 in the jaw 12 of the first clamping assembly. In the present embodiment there are two conical sections arranged, whereby the diameter of the bore 21 decreases with increasing length of the bore as seen from outside of the jaw 12. In case two conical sections 32 are present the degree of the pivoting motion can be increased.

The shaft 40 as part of a locking element is threaded into the lower jaw 11 of the second clamping assembly 30. Hence the lower jaw 11 comprises a threaded opening. Threading may be provided in the bore or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings.

Therefore the two clamp assemblies 20, 30 can be opened and closed through turning the head of shaft 40 and thus turning said shaft 40 in the jaw thread.

In the cross-sectional view of FIG. 3 it can also be seen that the locking element 40 extends through the first clamping assembly 20 and is in contact with the second clamping assembly 30 by means of the threaded portion 49. In mounting position in which the rods or pins will be positioned in the receptions 71, 72, 73 the first clamping assembly 20 is moveable along the middle axis M of the threaded portion 49. Upon actuation of the locking element 40 the first clamping assembly 20 will be moved against the spring pressure towards the second clamping assembly 30 such that the anti-rotation surface 55 of the first clamping assembly 20 comes into contact with the respective anti-rotation surface 55 of the second clamping assembly 30. Once the locking element 40 is firmly tightened the first clamping assembly 20 and the second clamping assembly 30 are in contact with each other via the anti-rotation surface 55.

In FIG. 2 the mounting position of clamping assemblies 20, 30 is shown. Thereby the clamping assemblies 20, 30 are positioned at the distance to each other with regard to the middle axis M. The second clamping assembly 20 is in contact with the locking element 40 and the spring 15 pushes the first clamping assembly away from the second clamping assembly 20 towards the washer 41 which is contact with the flange 45 of the locking element.

The clamping assemblies 20, 30 will be moved due to actuation of the locking element 40 from a mounting position to a locking position and afterwards when fixation shall be cancelled from the locking position to the mounting position. After use the washer 41 will be removed as explained below in order to sterilize the clamping element 10 for further use.

Figure 4:
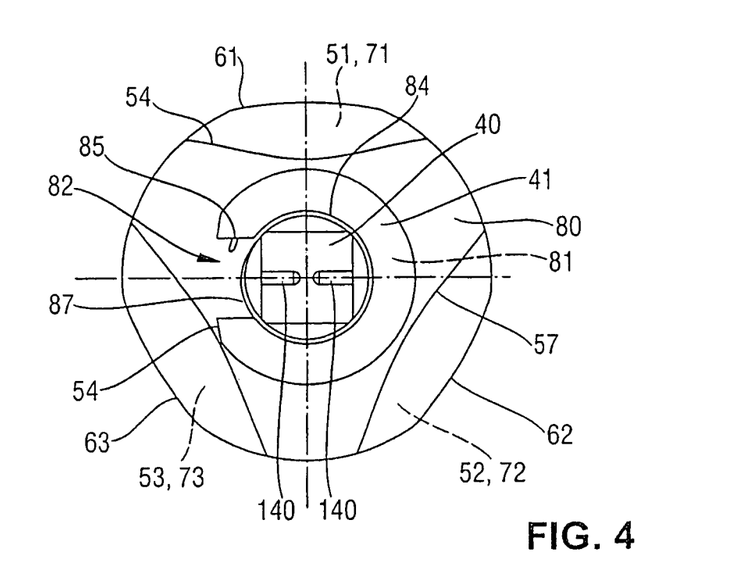
FIG. 4 shows a top view of the fixation clamp of FIG. 1.

FIG. 4 shows a view from above on the clamp according to FIG. 1. Since the embodiment of FIG. 1 comprises three grooves 51, 52 and 53, there are three side walls 61, 62 and 63, which provide, when looked from above as in FIG. 2 a triangular shape of each clamping assembly 20 or 30.

In the present embodiment the first clamping assembly 20 here the jaw 11 comprises a first contact surface 80 which is in contact with a second contact surface 81 of the washer 41. The washer 41 and the first clamping assembly 20 are in contact via said contact surfaces 80, 81. The contact surfaces 80, 81 are spherical having the same curvature radius such that the washer 41 is enabled to slide with respect to the first clamping assembly 20 on the contact surface 80 when it comes to the above mentioned pivoting motion of the first clamping assembly 20 with respect to the locking element 40. The curvature is at least the same over an overlapping surface which here is defined as the surface which encompasses the maximal gliding motion of the washer 41 on the contact surface 80.

In the present embodiment the first contact surface 80 has a convex shape, whereas the second contact surface 81 has a concave shape. Such a configuration is particularly advantageous as it allows a pivoting motion as mentioned above while providing a very compact structure of the fixation clamp in terms of axial and radial dimension. Furthermore the surfaces which are shaped as explained allow that the washer 41 as explained in detail below is removable from the clamping element 10. Thereby the first clamping assembly 20 and the second clamping assembly 30 become loose such that the parts are slightly moveable along middle axis M and sterilization of the clamping element 10 is possible without demounting the clamping element 10 completely. This is very advantageous since during sterilization the parts remain together and re-assembly of the parts afterwards is not necessary. Hence the parts of the clamping element 10 remain loosely together such that the sterilization fluid is able to enter clearances between the respective parts. As mentioned above providing the diameters D1 and D2 accordingly, the abutment surface 86 serves as element which holds the parts loosely together.

The first contact surface 80 of the first clamping assembly 20 extends from a section point 82 between the middle axis M of the locking element 40 and said first contact surface 80 towards the first clamping assembly 20.

FIG. 4 shows the clamping element from above showing the overlapping surface with limiting edges 54.

Figure 5:
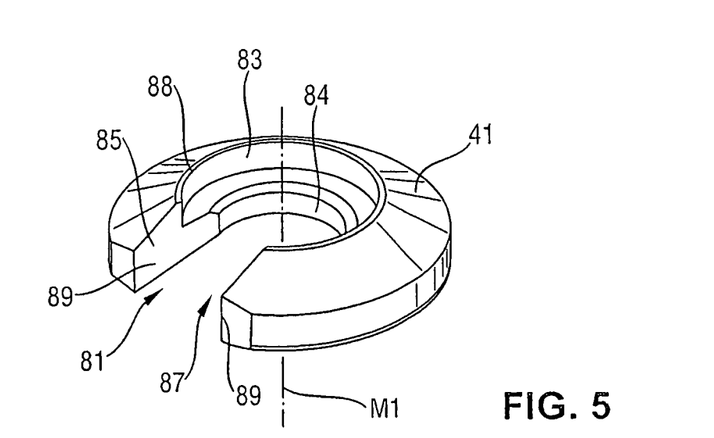
FIG. 5 shows a perspective view of a washer that is used in the fixation clamp of FIG. 1.

FIG. 5 shows the washer 41 in a perspective view. The washer is preferably made out of a metallic material. The washer comprises as mentioned above the contact surface 81 and an upper surface 88 which is arranged at a distance from the contact surface 81. A central through opening 84 having a middle axis M1 is partly circumvented by means of a sidewall. Said through opening extends from contact surface 81 to the upper surface 88. Locking element 40 is to be introduced through said through opening.

The sidewall is interrupted by cutout 87 which extends radially to the middle axis M1 through the sidewall to the opening 84 such that the sidewall becomes interrupted. The cutout 87 has a width which is slightly smaller than the reduced diameter portion 43 of the locking element 40 such that the washer 41 cannot be moved radially to the locking element 40 in order to remove the washer 41 after the use of the clamping element 10. The width is defined as the clearance of the cutout 87 from the surfaces 89 of the sidewalls 85 limiting the cutout 87. The corresponding feature on the shaft 40 to allow introduction and removal of the washer 41 is explained below.

Furthermore the washer 41 comprises a recess 83 extending along middle axis M1 from an upper surface 88 which is arranged opposite the contact surface 81. Said recess 83 extends from the upper surface 88 along the middle axis M1 of the through opening 84 into the washer 41. The recess 83 is designed to accommodate the flange 45 of the locking element 40. The recess 83 can also be designated as abutment element since it prevents that the washer can be radially displaced to the middle axis M of the locking element 40. In order to demount the washer it is necessary to push the first clamping assembly 20 towards the second clamping assembly 30, such the washer 41 can also be moved along the middle axis M of the locking element 40. Thereby the flange 45 will be moved out of the recess 83. Once the flange 45 has been moved such that there is no connection between the flange 45 and the recess 83, the washer 41 can be moved, if correctly aligned as explained below, radially to the locking element 40 whereby the shaft of the locking element will pass the cutout 87 of the washer.

As can be seen in FIG. 5 the sidewalls 85 are parallel to a plan comprising the middle axis M1 and a radial direction extending from said middle axis M1. In other words, the opening of the cutout 87 is a rectangular opening having a predetermined distance of the two surfaces 89 of the sidewalls over the whole cutout 87. The diameter of the circular through opening 84 is larger than that predetermined distance. Therefore the washer 41 cannot be easily pushed radially from the reduced diameter 43 portion of the circular shaft 40 if said diameter fits into the through opening 84.

Figure 6:
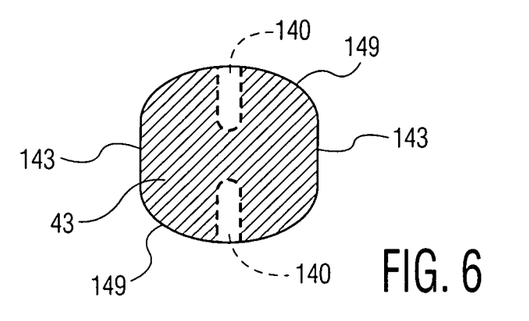
FIG. 6 shows a cross-sectional view of the flattened area of the locking element shaft.

In order to allow this introduction of the washer, as shown in FIG. 1, the reduced diameter portion 43 of the shaft 40 is provided with two flat portions 143 shown in FIG. 6; i.e. the round surface of the shaft 40 is beveled for a predetermined distance along axis M which is at least as long as the height of the sidewalls 85 of the washer 41. The distance between the two opposite and parallel flat surfaces 143 is a predetermined small amount smaller than the distance between the sidewalls 85 of the cutout 87 of the washer 41.

As can be seen in FIGS. 1 and 4, the head portion 44 of the shaft 40 is provided with two grooves 140 being oriented parallel to the parallel flat surfaces 143. These grooves 140 are markings allowing the user to orient the washer 41 in a correct way to allow its introduction or removal. In fact, the two opposite directions provided by the markings 140 explain the user to orient the cutout 87 of the washer 41 in this direction to orient the cutout 87 in the direction of the beveled or flattened surfaces 143 providing the necessary reduced diameter portion for introduction of removal of the washer onto the shaft 40.

The removable washer 41 has the advantage that the clamping assemblies 20, 30 become moveable along the interlocking element 40 such that an effective sterilization becomes possible. The beveled or flattened surface 143 together with the reduced distance cutout (compared to the through opening diameter) provide an orientation means to help the user as follows disassembling the coupling. Initially the coupling is opened. Then the slot or cutout 87 of the washer 41 is aligned with the markings 140 at the screw head 44. These markings which comprise preferably a radial line which can be symmetrical, separated into two notches as in the shown embodiment etc., indicate the user that the washer 41 can only be removed with this specific alignment. This is already reflected in FIG. 1, since shaft 40 is in the correct orientation in view of the cutout 87 of washer 41 of FIG. 1, shown after compression of the coupling allowing the removal of the washer. Releasing the coupling than allows to push the uppermost jaw into a favorable position for cleaning, since diameter D1 of bore 21 is larger than flange 45; but diameter D2 is not.

Insertion of the washer 41 is the other way round. Initially the coupling is fully unscrewed and extended. The coupling is then compressed, i.e. the assemblies 20 and 30 are pushed one against the other, compressing spring 15 and showing the reduced diameter portion 43 as in FIG. 1. The washer 41 is inserted in the only possible orientation while the notches 140 at the screw head are in parallel to the cutout 87 of the washer. Releasing the coupling moves the recess 83 into the flange 45 thus fixing the height position of the washer 41 which is no longer at the height of the beveled surfaces 143 of the reduced diameter portion 43. Preferably, the beveled surfaces 143 extend in the longitudinal direction M1 of the fixation clamp 10 over the entire length of the reduced diameter portion 43, so that there is no need for a specific introduction or removal height of the washer 41.

Figure 7:
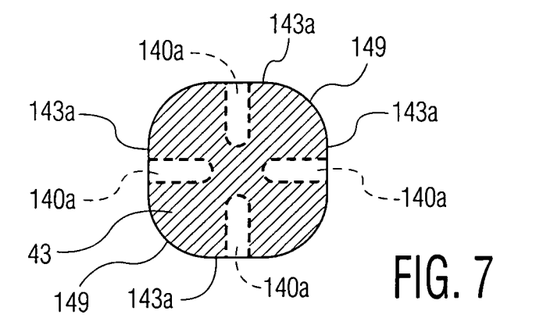
FIGS. 7, 8 and 9 show alternate cross-sectional views of the flattened area of the locking element shaft.
Figure 8:
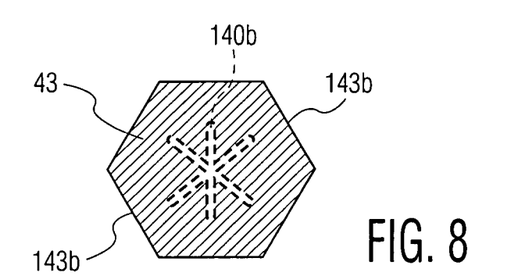
Figure 9:
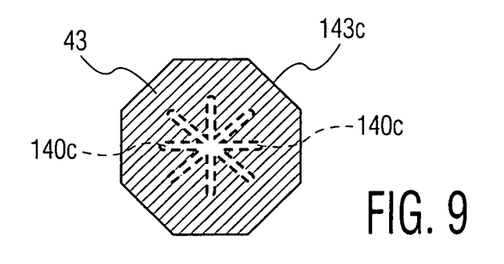

In a different embodiment according to the invention, it is possible to provide more than one pair of beveled surfaces 143 on the locking element 40. It is possible to provide two times two (four) surfaces 143a of FIG. 7, creating a square cross section of the reduced diameter portion 43 so that four removal positions of the washer 41 at 90 degrees intervals are provided. It is also possible to provide three pairs 143b of FIG. 8, forming a hexagonal cross section with 60 degrees intervals for the removal, or four pairs 143c forming an octagon, etc. Between adjacent beveled surfaces circular portions 149 of the shaft section 43 can remain, thus changing the cross section (square, hexagon, octagon) into a polygon of straight portions and circular arc portions. Of course the number and the orientation of the markings 140 on the head portion 44 have to follow, providing a cross of markings for the four-sided-solution and a six-pointed star for the hexagonal beveled surfaces 143. When there are provided two, three or four pairs of beveled surfaces 143, 143a, 143b and 143c of FIG. 9, they form an angle of 90°, 60° and 45°, respectively, between adjacent surfaces in a cross section view, forming a partly square, hexagonal or octagonal cross section, optionally with circular arc portions 149 between the straight portions relating to the beveled surfaces 143. Markings 140a, 140b and 140c are shown in FIGS. 7, 8, and 9 are similar to marking 140 showing the orientation of the flat or beveled surfaces.

Beside the markings 140, 140a, 140b, and 140c on the upper surface on the head 44 of the locking element 40, e.g. as grooves or ridges, indicating the direction of one or the pair of beveled surfaces (143, 143a, 143b, and 143c as shown in the embodiment in the drawings, it is possible to provide one or more markings on a side surface of the head 44 of the locking element, where the cutout 87 portion of the washer 41 is to be positioned to be inserted or removed, e.g. one of the four side surfaces of the head 44 of the embodiment of FIG. 1 can be marked in a specific different color or have a specific surface appearance other than the other side surfaces of the head 44.

The arrangement of the contact surfaces 80, 81 has the advantage that during the mounting process of the fixation clamp 10 a pivoting motion of the first clamping assembly becomes possible with a large deflection.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation clamp for use in an external fixation system for holding bone fragments adjacent to each other with the help of fixation elements, comprising
   at least one clamping assembly having at least one reception to accommodate a fixation element along a longitudinal axis of the reception and at least one locking element extending through a bore in the clamping assemblies for blocking the position of the clamping assemblies in a defined angular position,
   a washer arranged between a head portion of the locking element and one clamping assembly,
   wherein the washer comprises a central through opening having a first diameter centered around a middle axis, the through opening surrounded by an area recessed from an outer surface of the washer which extends transverse to the middle axis, the recessed area having a cross-section larger than the first diameter, wherein said locking element extends through said through opening, the washer having a cutout defining parallel planar sidewalls extending radially to said middle axis of said through opening such that said washer is mountable and demountable in an essential radial direction to the middle axis of the locking element, wherein the cutout has a smaller distance between its sidewalls than the diameter of the through opening,
   wherein the locking element has a first circular cross-section below its head portion adapted to fit through the through opening of the washer but larger than the opening of the cutout and comprises at least one pair of planar surfaces oriented in parallel one to the other and having a distance one from the other being smaller than the distance between the planar sidewalls of the cutout of the washer, the distance between the planar sidewalls of the washer being larger than the distance between the locking element planar surfaces prior to engagement therewith, the locking element having a second cross-section extending between the head portion and the first circular cross-section, the second cross-section larger than the first circular cross-section and adapted to be received in the washer recessed area.

2. The fixation clamp according to claim 1, wherein the head of the locking element comprises a marking indicating the direction of one or the pair of beveled surfaces where the cutout portion of the washer is to be positioned to be inserted or removed.

3. The fixation clamp according to claim 2, wherein the marking on the head of the locking element is provided on the upper surface of the head of the locking element.

4. The fixation clamp according to claim 1, wherein the head of the locking element comprises one or more markings on one or more side surfaces of the head, where the cutout portion of the washer is to be positioned to be inserted or removed.

5. The fixation clamp according to claim 4, wherein the markings on the side surface(s) of the head have a specific different color than the other side surfaces.

6. The fixation clamp according to claim 1, wherein there are provided two pairs of planar surfaces forming an angle of 90° between adjacent surfaces in a cross-sectional view, forming a partly square cross-section.

7. The fixation clamp according to claim 6, wherein circular arc portions are provided between the straight portions of the pairs of planar surfaces.

8. The fixation clamp according to claim 1, wherein there are provided three pairs of planar surfaces forming an angle of 60° between adjacent surfaces in a cross-sectional view, forming a partly hexagonal or octagonal cross-section.

9. The fixation clamp according to claim 1, wherein there are provided four pairs of planar surfaces forming an angle of 45° between adjacent surfaces in a cross-section view, forming a partly octagonal cross-section.

10. The fixation clamp according to claim 1, wherein the locking element comprises a flange which is in contact with said washer.

11. The fixation clamp according to claim 1, wherein said washer is dismountable in a direction substantially perpendicular to said locking element upon movement of the clamping assembly axially along the locking element.

12. The fixation clamp according to claim 1, wherein said clamping assembly comprises a first contact surface which is spherical and convex and wherein said washer comprises a second contact surface which is spherical and concave, wherein the first contact surface is in contact with the second contact surface, and wherein the concave surface is complementary to the convex surface.

13. The fixation clamp according to claim 12, wherein the first contact surface of the clamping assembly extends from a section point between the middle axis of the locking element and said first contact surface towards the clamping assembly.

14. The fixation clamp according to claim 12, wherein the radius of curvature of the first and second contact surfaces is constant at least with respect to the overlapping surface between the first contact surface of the clamping assembly and the second contact surface of the washer.

15. The fixation clamp according to claim 12, wherein the bore comprises, towards the first contact surface, a first diameter which is adjoined by a second diameter, wherein the first diameter is larger than the second diameter such that between the first and the second diameter an abutment surface is provided, which abutment surface serves as abutment element for the locking element, in particular for the flange, in case the washer is removed.

16. The fixation clamp according to claim 1, wherein the clamping assembly bore through which said locking element extends, comprises a diameter that is larger than the diameter of the locking element in the respective region and wherein at least parts of the clamping assembly are pivotable against the locking element.

17. The fixation clamp according to claim 16, wherein the bore comprises at least one conical section such that the clamping assembly is pivotable against the locking element.

18. The fixation clamp according to claim 1, wherein the bore comprises at least partly a diameter that is smaller than the diameter of a flange of the locking element.

19. The fixation clamp according to claim 1, wherein each clamping assembly comprises two jaws, wherein each jaw comprises a number of grooves to form said receptions with the corresponding jaw.

20. The fixation clamp according to claim 19, wherein between the clamping assemblies a spring element is arranged providing a force along the locking element.

21. The fixation clamp according to claim 1, wherein as seen along the locking element, a first clamping assembly is followed by at least a second clamping assembly, wherein the locking element is in contact with the second clamping element by means of a thread and wherein locking element extends through the first clamping assembly wherein a spring provides an axial force onto the first clamping assembly which is pushed against said washer.

22. The fixation clamp as set forth in claim 1 wherein a spring element is mounted on the locking element and biases the washer towards the locking element head portion.

23. The fixation clamp as set forth in claim 22 wherein when mounted the washer recessed area is biased into contact with the locking element second cross-section.

24. A fixation clamp for use in an external fixation system for holding bone fragments adjacent to each other with the help of fixation elements, comprising:
a clamping assembly having a reception to accommodate a fixation element extending along a first longitudinal axis of the reception and at least one locking element extending through the clamping assemblies for blocking the position of the clamping assemblies in a defined angular position, the locking element having a head portion and a shaft portion with the shaft portion extending therefrom along a second longitudinal axis,
a washer arranged between the locking element head portion and the clamping assembly,
wherein the washer comprises a central through opening having a first diameter centered around a middle axis, the through opening surrounding by an area recessed from an outer surface of the washer extending transverse to the middle axis, the recessed area having a cross-section larger than the first diameter, wherein said locking element extends through said central opening, and a cutout defining planar sidewalls portion extending in a radial direction to said middle axis of said through opening such that said washer is mountable and demountable in a radial direction to the middle axis of the locking element, wherein the cutout has a smaller distance between the planar sidewalls than the diameter of the through opening,
wherein the locking element shaft portion has a first circular cross-section below its head portion adapted to fit through the through opening of the washer but larger than the opening of the cutout, the shaft portion further comprises at least one pair of flattened surfaces oriented parallel to one another separated by a distance one from the other which is smaller than the distance between the planar sidewalls of the cutout of the washer, wherein the head of the locking element comprises a marking indicating the direction of the parallel flattened surfaces indicating where the cutout portion of the washer is to be positioned for insertion or removal, the distance between the planar sidewalls of the washer being larger than the distance between the locking element planar surface prior to engagement therewith, the locking element having a second cross-section extending between the head and the first circular cross-section, the second cross-section larger than the first circular cross-section and adapted to be received in the washer recessed area.

* * * * *